US009498556B2

(12) United States Patent
Hancock et al.

(10) Patent No.: US 9,498,556 B2
(45) Date of Patent: *Nov. 22, 2016

(54) DIAPER TO TREAT DIAPER RASH

(71) Applicant: Bum Bum Diapers, LLC, Dallas, TX (US)

(72) Inventors: Cheryl Hancock, Dallas, TX (US); Melanie Youschak, Key West, FL (US); Carlos Richer, Garza Garcia Nuevo Leon (MX)

(73) Assignee: Bum Bum Diapers, LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/856,327

(22) Filed: Sep. 16, 2015

(65) Prior Publication Data

US 2016/0213805 A1    Jul. 28, 2016

Related U.S. Application Data

(60) Provisional application No. 62/162,429, filed on May 15, 2015, provisional application No. 62/143,539, filed on Apr. 6, 2015, provisional application No. 62/108,418, filed on Jan. 27, 2015.

(51) Int. Cl.
*A61K 8/02*     (2006.01)
*A61L 15/44*    (2006.01)

(52) U.S. Cl.
CPC .............. *A61L 15/44* (2013.01); *A61K 8/0204* (2013.01); *A61L 2300/102* (2013.01); *A61L 2300/22* (2013.01); *A61L 2300/30* (2013.01)

(58) Field of Classification Search
CPC .................................................... A61K 8/0204
See application file for complete search history.

(56) References Cited

U.S. PATENT DOCUMENTS

| 7,771,735 | B2 | 8/2010 | Dvoracek et al. |
| 2002/0058056 | A1* | 5/2002 | Yahiaoui ............... A61F 13/511 424/402 |

* cited by examiner

*Primary Examiner* — Carlos Azpuru

(57) ABSTRACT

A package of diapers is provided for treating diaper rash, where the package of diapers includes a first diaper and a second diaper. The first diaper includes an absorbent layer configured to absorb moisture away from a wearer of the first diaper and a topical layer applied on the absorbent layer of the first diaper in a first pattern. The second diaper includes an absorbent layer configured to absorb moisture away from a wearer of the second diaper and a topical layer applied of the absorbent layer of the second diaper in a second pattern, where the first pattern is different than the second pattern.

14 Claims, 7 Drawing Sheets

DIAPER TO TREAT DIAPER RASH

CROSS-REFERENCE TO RELATED APPLICATIONS

The present application is related to the subject matter of U.S. Provisional Application No. 62/108,418 entitled "DIAPER TO TREAT DIAPER RASH," filed on Jan. 27, 2015, U.S. Provisional Application No. 62/143,539 entitled "DIAPER TO TREAT DIAPER RASH," filed on Apr. 6, 2015, U.S. Provisional Application No. 62/162,429 entitled "DIAPER TO TREAT DIAPER RASH," filed on May 15, 2015. The content of the above-identified patent documents is incorporated herein by reference.

TECHNICAL FIELD

The present application relates generally to diapers and, more specifically, to a diaper for treating diaper rash.

SUMMARY

For a more complete understanding of the present disclosure and its advantages, reference is now made to the following description taken in conjunction with the accompanying drawings, in which like reference numerals represent like parts:

Various embodiments provide a package of diapers for treating diaper rash. The package of diapers includes a first diaper and a second diaper. The first diaper include an absorbent layer configured to absorb moisture away from a wearer of the first diaper and a topical layer applied on the absorbent layer of the first diaper in a first pattern. The second diaper includes an absorbent layer configured to absorb moisture away from a wearer of the second diaper and a topical layer applied of the absorbent layer of the second diaper in a second pattern, where the first pattern is different than the second pattern.

Various embodiments provide a diaper for treating diaper rash including an absorbent layer configured to absorb moisture, a topical layer comprising 25% by weight of organic shea butter, 25% by weight of pure white beeswax, and a plurality of specialized ingredients.

Various embodiments provide a method for manufacturing a plurality of diapers. The method including feeding a wax substance that is pressurized for use in a topical layer over a protective area for each of a plurality of diapers, where, the protective area is positioned on each of the plurality of diapers in a manner for consistent application on a wearer. The method also includes applying the wax substance in a first pattern on a protective area of a first diaper. The method further includes applying the wax substance in a second pattern on a protective area of a second diaper, where the first pattern is different than the second pattern.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; and the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 8, discussed below, and the various embodiments used to describe the principles of the present disclosure in this patent document are by way of illustration only and should not be construed in any way to limit the scope of the disclosure. Although a baby is used as a reference throughout the disclosure, the diaper can be worn by any wearer that is dealing with diaper rash or any other related condition.

Irritant diaper dermatitis, more commonly known as diaper rash, occurs in infants and children, but can also affect people who are incontinent, paralyzed, or bedridden. Some causes of diaper rash include friction from the skin rubbing against the wet diaper, irritation from prolonged exposure to feces, urine, or other chemicals produced with the diaper, allergic reactions to materials produced or added to the diapers, and fungal or yeast infections. Symptoms of diaper rash including red or irritated skin are easily identified on the skin in contact with diaper. Typical treatment of diaper rash includes cleaning, use of various creams, and air drying the affected area, which sometimes requires leaving the diaper off for extended periods of time.

Many times when dealing with diaper rash there is not enough time for the normal recommended treatment of cleaning and allowing the affected area to dry, which is also not a very good option for babies who are not potty trained. Leaving the diaper rash untreated potentially leads to making the rash worse or increasing the likelihood of developing a level 2 diaper rash, including a yeast or other infections. Several approaches to address the issue include different treatment options, such as absorbent materials or a topical remedy, including creams and powders, for diaper rash. Absorbent materials are designed to remove as much wetness from the surface layer of the diaper in contact with the skin. The creams are designed to act as barriers, and the powders were designed to neutralize the pH of urine to reduce the acidity contact with the skin. These solutions add significant weight when being transported; increasing the challenge for a mom or health care specialist on the go, especially when diaper rash is not present and the solutions are not needed. One example embodiment is to take existing treatments of either powders or creams and incorporate them within the diaper or pad. However, creams create conditions prime for mold growth, and both powders and creams at times leak into the packaging, diaper bag, car seat, clothes, or basically anything with which the diaper comes into contact.

Figure 1:
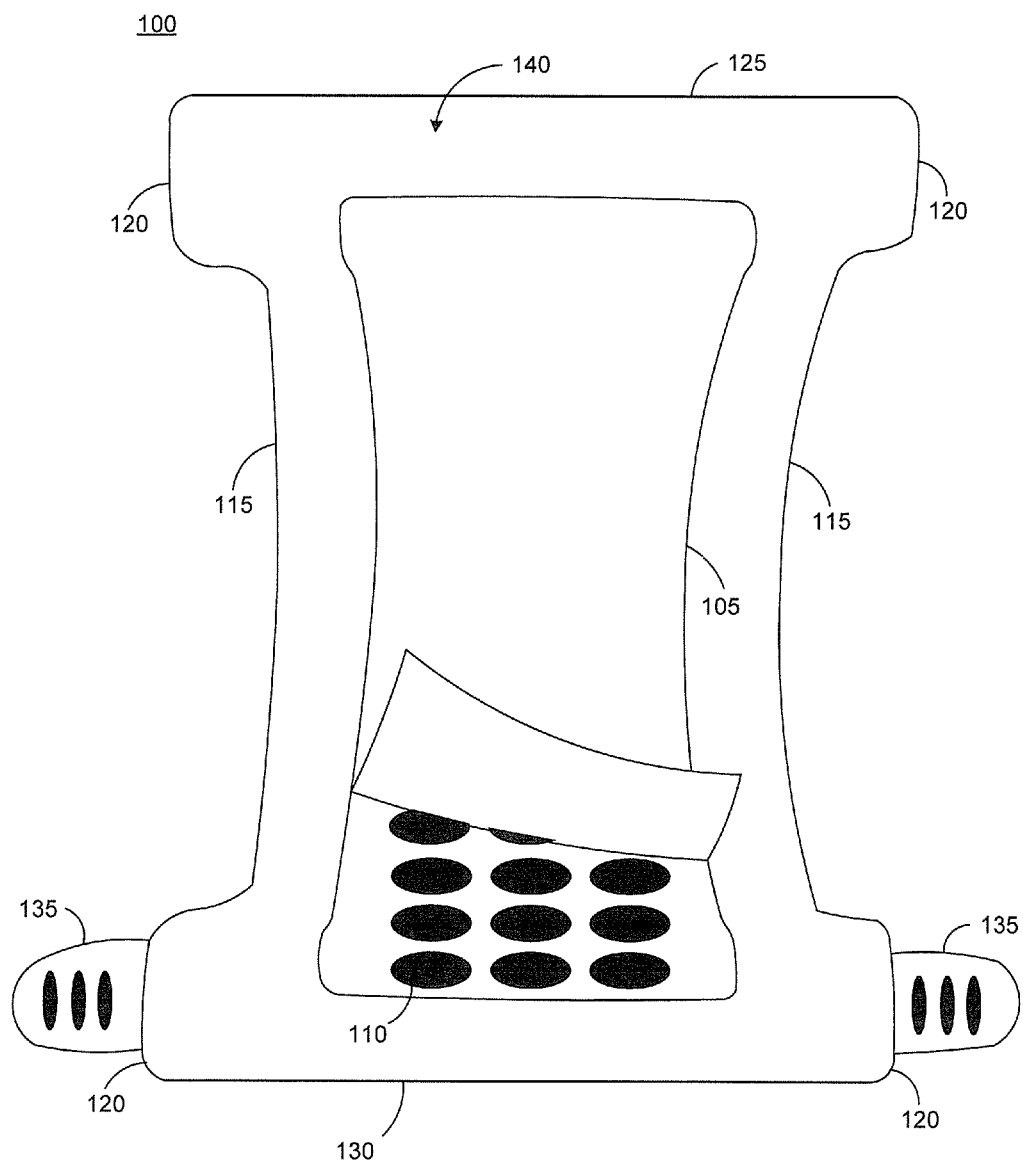
FIG. 1 illustrates a top view of a diaper with a portion of an enclosing layer separated from the diaper exposing the topical layer according to one embodiment of the present disclosure.

FIG. 1 illustrates a top view of a diaper 100 with a portion of an enclosing layer 105 separated from the diaper 100 exposing the topical layer 110 according to one embodiment of the present disclosure. The topical layer 110 can be defined as a composition, topical composition, permeable liner, or absorbent layer. The diaper 100 shown in FIG. 1 is for illustration only. Other embodiments could be used without departing from the scope of the present disclosure.

The diaper 100 is substantially rectangular in shape with the length concave for leg lining 115, located at center along both of the longer sides of the diaper 100, and four tabs 120, one located at each side of the front end 125 and the back end 130, meant for supporting and enclosing the diaper 100 around the wearer. The diaper 100 also includes two fasteners 135, one located on each of the tabs 125 on the back end 130, meant for securing the diaper 100 on the wearer. The fasteners 135 are for connecting to the tabs 120 located on the front end 125 of the diaper meant to hold the tabs 120 together around the wearer. The fasteners 135 are illustrated as sticky tabs, but can be any fastening method such as tape, clothes pins, etc. The center of the diaper 100 contains a topical layer 110 covered by an enclosing layer 105. The enclosing layer 105 is comprised of a thin layer of light plastic-like material meant for enclosing and protecting the topical layer 110.

Figure 2:
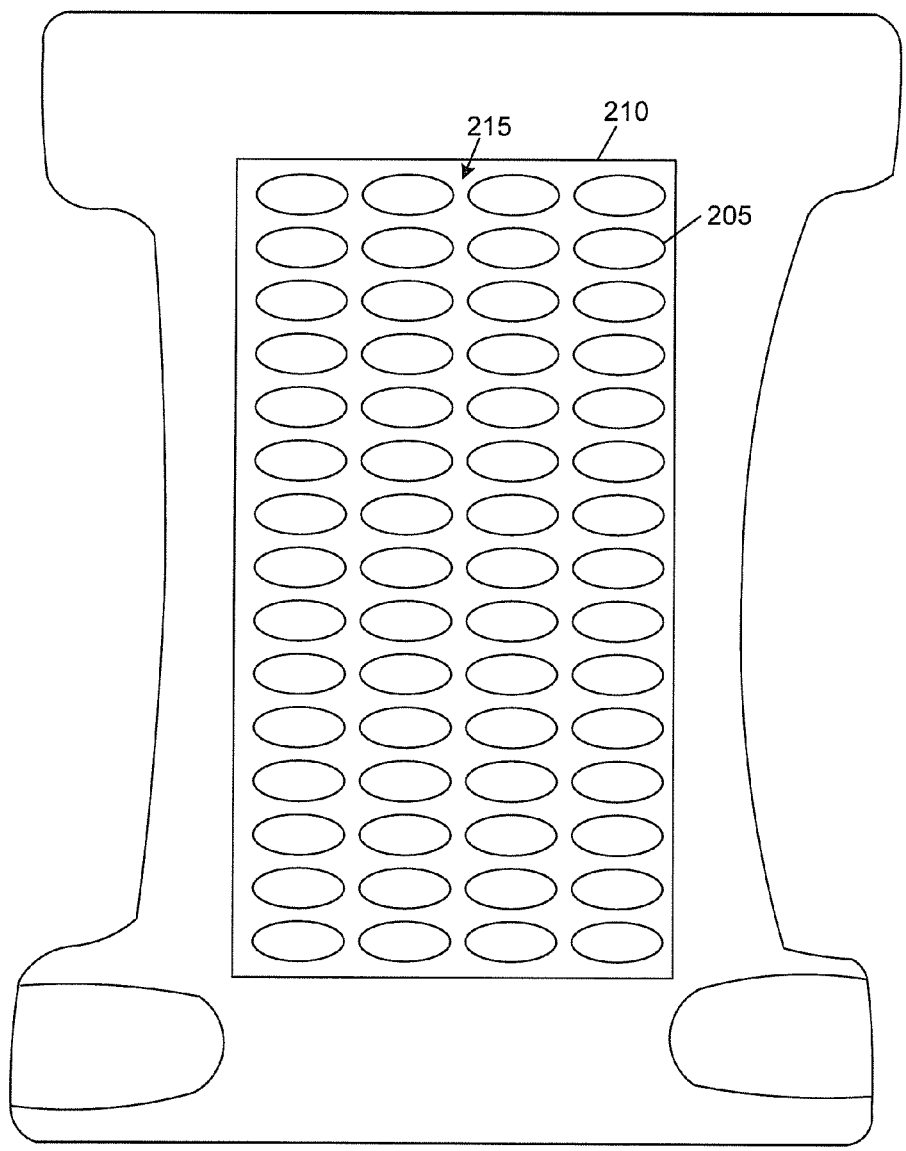
FIG. 2 illustrates an embodiment of the topical layer applied on an absorbent layer of a diaper in accordance with disclosed embodiments.
Figure 3:
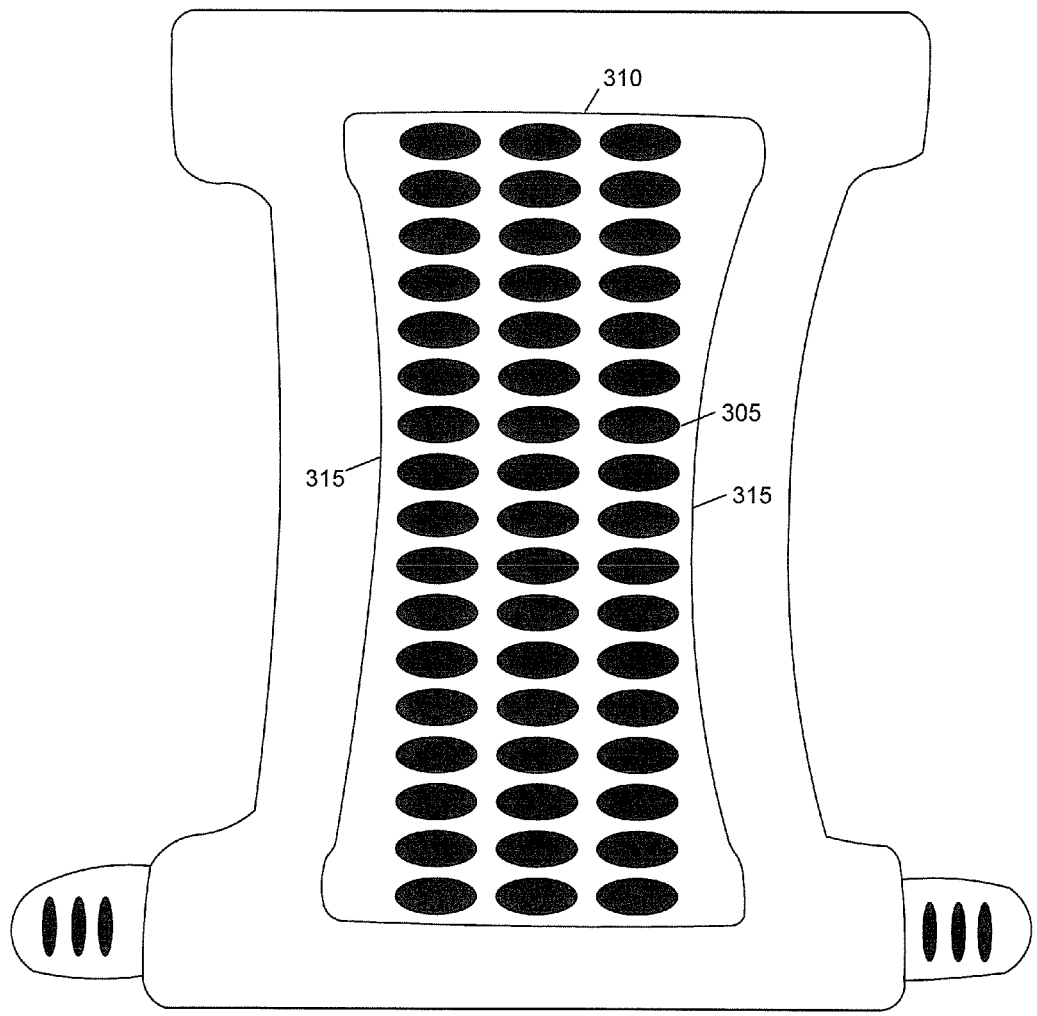
FIG. 3 illustrates an embodiment of the topical layer applied on an absorbent layer of a diaper in accordance with disclosed embodiments.

The topical layer 110 is comprised of a thin layer of wax or a wax-like substance. The wax or wax-like substance can be a dry wax that is capable of melting at a desired temperature. The topical layer 110 covers a half or slightly more than half of the diaper 100 and can be structured in different shapes, as illustrated in FIGS. 2 and 3. The topical layer 110 is formed on the chassis 140 of the diaper 100, separate from any absorbent layers. In certain embodiments, the topical layer 110 is an insert that can be attached or placed inside any type of diaper or pad.

The topical layer 110 is meant to have a solid form at ambient temperature, but a low melting point or high viscosity. The wax is meant to stay in solid form when the diaper 100 is not in use, but melts upon heating from the body temperature of the wearer due to the contact with the wearer and spreads on the wearer using friction of the body against the topical layer 110. Remaining in the wax form prevents the diapers 100 from creating an environment for mold to grow and reduces the possibility of leakage. The topical layer 110 can be formed in a solid layer, a patterned layer, a plurality of individual shapes, or distributed in any fashion. The distribution of the topical layer 110 is structured to optimize the location of the wax and also to provide flexibility for reduction of any material breaking off and causing a mess. The topical layer 110 can also be structured with a variable thickness. Furthermore, the amount of wax used is minimal compared to the weight of a cream or powder, allowing both greater comfort for the wearer of the diaper 100 and reduced hauling weight for the caregiver. The topical layer 110 also adds a minimal thickness to the diaper 100 to where the added thickness is negligible, which also increases the comfort for the wearer. The minimal thickness also allows the caregiver to pack more diapers 100 for longer outings, maintain a lighter weight of a diaper bag, or increases the amount of storage space.

In certain embodiments, the topical layer 110 is comprised of organic Shea butter and pure white beeswax. Along with those initial ingredients, the topical layer 110 includes specialized ingredients. In different example embodiments, for preventative care, the topical layer 110 can include 16%-40% zinc oxide powder, liquid lanolin (pure emollient oil), organic dandelion root powder, and chickweed herb powder. For sensitive skin, the topical layer 110 can include 16%-40% zinc oxide powder, liquid lanolin (pure emollient oil), organic aloe vera powder, and chamomile flowers. For corrective care, the topical layer 110 can include up to 40% zinc oxide powder, liquid lanolin (pure emollient oil), cod liver oil, and chamomile flowers powder. For overnight care, the topical layer 110 can include 16%-40% zinc oxide powder, organic lavender oil, and chamomile flowers powder.

In yet further embodiments, the topical layer 110 can include 40% zinc oxide powder, cod liver oil, chickweed herb powder, liquid lanolin, and dandelion root powder.

In one or more of the embodiments of this disclosure, the topical layer 110 can include:
 25% by weight of Shea Butter;
 25% by weight of pure white beeswax;
 2% by weight of chickweed herb powder;
 2% by weight of dandelion root powder;
 40% by weight of zinc oxide powder;
 4% by weight of cod liver oil; and
 2% by weight of liquid lanolin.

In one or more of the embodiments of this disclosure, the topical layer 110 can include:
 25% by weight of Shea Butter;
 25% by weight of pure white beeswax;
 2% by weight of chickweed herb powder;
 2% by weight of dandelion root powder;
 40% by weight of zinc oxide powder;
 3% by weight of cod liver oil; and
 2% by weight of liquid lanolin
 1% by weight of phenonip.

The example topical layers can include other inactive or active ingredients.

In other example embodiments, the range of percentages can be different. This list of different formulas and specialized ingredients is not exhaustive and for illustration of different possible uses. Furthermore, the specialized ingredients can be used for other purposes than described. The formulas and ingredients are designed to create a combination of a calming effect on diaper rash and to only activate when the temperature of the wax is raised above the ambient temperature. The ingredients are melted together in the liquid form, applied or stamped into the chassis of the diaper, and then cooled back into a wax or wax-like form once in place.

In an example embodiment, the topical layer can be sent to a diaper manufacturer in drums, such as fifty-five gallon drums. There can be a heat jacket that fits over each drum, warming a solid form of the topical layer from a wax-like state into a liquid state. The topical layer can then be applied to a top woven layer using a straight line machine. In different embodiment, a zebra pattern can be used for application or other pattern type. In one or more embodiments, the pattern used may be used to prevent thickness during melting.

In one embodiment, a diaper manufacturer can apply around five grams of topical layer per diaper and spiral the top woven layer in large quantities.

FIG. 2 illustrates a top view of a diaper 200 with the topical layer 205 applied on an absorbent layer 210 in a rectangular shape according to various embodiments of this disclosure.

Diaper 200 includes a protective area 215. The protective area 215 is defined by the absorbent layer 210 in FIG. 2 is for illustration purposes only and can be a specific area or multiple areas of the absorbent layer 210. The protective area 215 can be determined based on areas of the diaper with the highest possibility of diaper rash for the wearer. For convenience of discussion, the protective area is illustrated as the area of the absorbent layer.

FIG. 3 illustrates a top view of a diaper 300 with the topical layer 305 on an absorbent layer 310 in a rectangular shape with concave sides 315 along the length of the diaper 300 according to one embodiment of the present disclosure.

Figure 4:
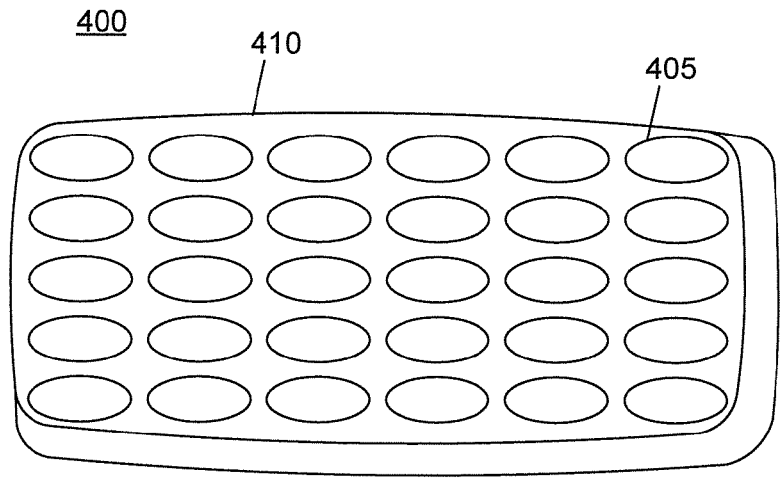
FIG. 4 illustrates an embodiment of the topical layer applied on an absorbent layer of a pad in accordance with disclosed embodiments.

FIG. 4 illustrates a top view of a pad 400 in a rectangular shape with a topical layer 405 on the absorbent layer 410 according to one embodiment of the present disclosure.

Figure 5:
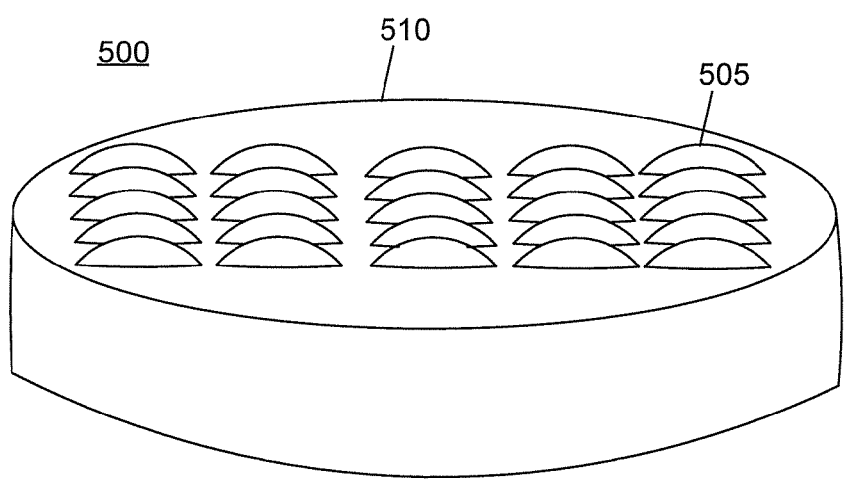
FIG. 5 illustrates an embodiment of the topical layer applied on an absorbent layer of a pad in accordance with disclosed embodiments.

FIG. 5 illustrates a side view of a pad 500 in a cylindrical shape with a topical layer 505 on the absorbent layer 510 according to one embodiment of the present disclosure.

FIGS. 2-5 illustrate different embodiments of the topical layer in accordance with disclosed embodiments. The embodiments shown in FIGS. 2-5 are for illustration only. Other embodiments could be used without departing from the scope of the present disclosure. The topical layers are illustrated as domes evenly spaced across the absorbent layers, but any shapes or patterns can be used to pattern the topical layer. For example, the topical layers can be shaped with a flat top surface, as a dome structure, or irregularly. The shapes can be different for each row, column or While the pattern in FIG. 4 is illustrated as covering the entire absorbent layer, different patterns can be applied to partial areas of the absorbent layer as illustrated in FIG. 5 with the pattern in a horizontal strip across the pad.

The pads or diapers themselves can comprise different shaped surfaces for optimal use of the topical layer. The diapers or pads include different thickness for holding or concentrating the wax after melting from use. For example, the thickness at the center of the pad can be reduced from the outside edges of the pad.

Figure 6:
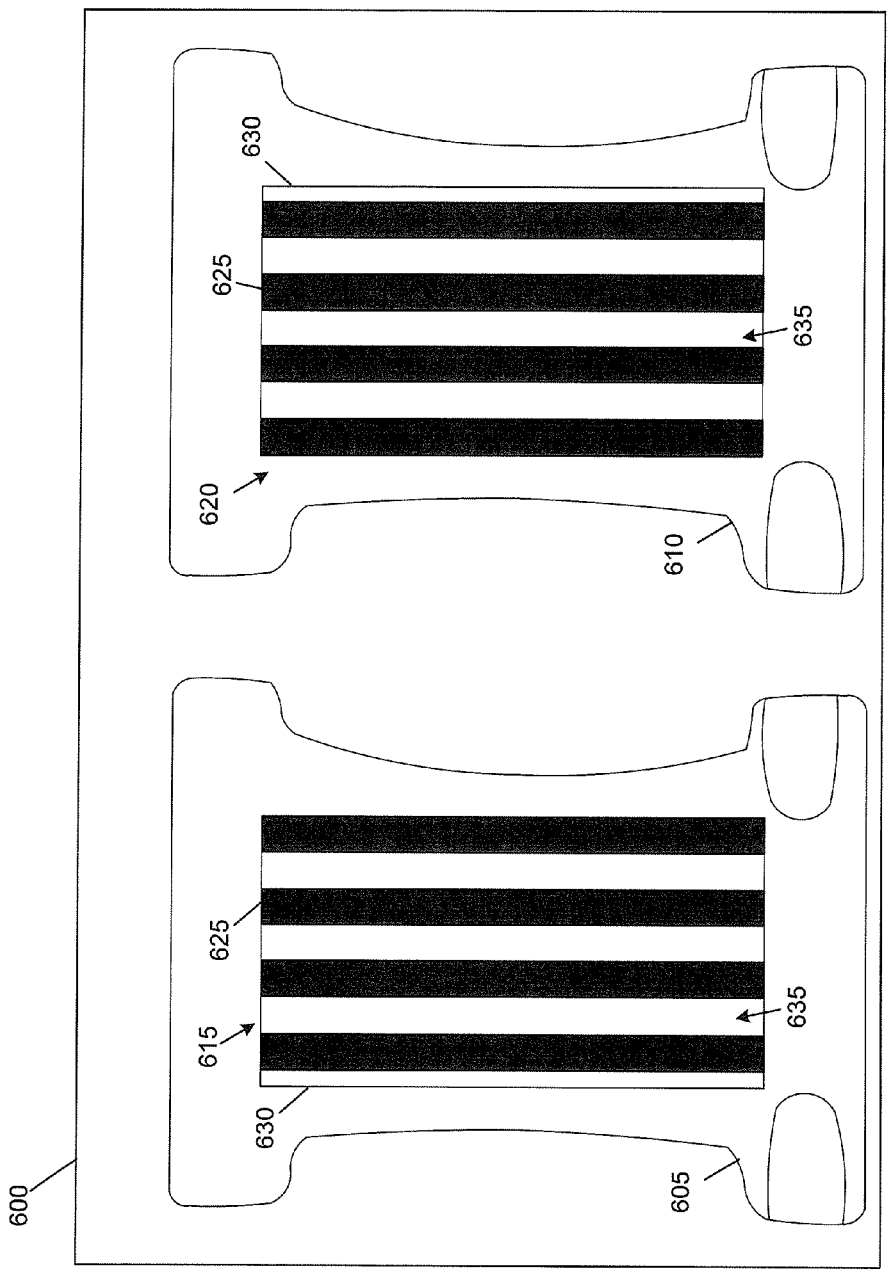
FIG. 6 illustrates different patterns on diapers packaged together in accordance with disclosed embodiments.

FIG. 6 illustrates a first pattern 615 on a first diaper 605 and a second pattern 620 on a second diaper 610 in a package 600 together in accordance with disclosed embodiments. While FIG. 6 illustrates two diapers in a package, any amount of diapers can be included in a package. While FIG. 6 illustrates two diapers in an open position, the diapers may be folded or stored in any manner. The diapers may also be packed in any type of packing, such as, but not limited to, a plastic wrap packaging, a cardboard box, a box of recycled material, and the like.

In certain embodiments, the topical layer 625 is hydrophobic requiring selective application on the absorbent layer 630. The topical layer 625 being applied in a pattern and not across the entire absorbent layer 630 allows the absorbent layer 630 to absorb any moisture found in the diaper. Because the topical layer 625 is composed of a hydrophobic material, applying the topical layer 625 across the entire absorbent layer 630 could trap the moisture on the skin of the wearer of the diaper.

Along with providing a barrier, the topical layer 625 also provides soothing benefits to the wearer of the diaper and needs to be applied across the entire protective area 635. The protective area 635 can be across the entire surface of the absorbent layer 630 or focused on the highest problem areas for diaper rash.

For maximum effectiveness to the wearer, the entire protective area 615 could be covered over a plurality of diapers. In other words, the topical layer 625 is applied in different patterns on the protective area 635 of each diaper in a pack 600 of diapers in order for the topical layer 625 to affect the entire troubled region on the wearer. In different embodiments, the protective area 615 could cover the entire absorbent layer or could be smaller than the area of the absorbent layer.

FIG. 6 illustrates a pack 600 including a first diaper 605 and a second diaper 610. The first diaper 605 and the second diaper 610 include the same protective areas 635, but have the topical layer 625 applied in a first pattern 615 and a second pattern 620. The first pattern 615 and the second pattern 620 are different in order to allow moisture to pass to the absorbent layer 630, while covering the entire troubled area between using both the first diaper 605 and the second diaper 610 found in together in pack 600. In some embodiments, the entire protective area 615 is covered by using more than two diapers.

In one or more embodiments, the first pattern 630 and second pattern 620 overlap. In other embodiments, the patterns 620 and 630 do not overlap. When using the term overlapping, the patterns do not physically overlap one another, but cover at least some of the same areas of the corresponding diaper for each pattern. For example, if two patterns overlap, both may cover the top portion of the protected area for the corresponding diaper for each pattern.

While both the first pattern 615 and the second pattern 620 illustrated are patterned as stripes along the length of the diapers, the patterns can be applied in any shape or design, such as a matrix of dots. Furthermore, the stripes are illustrated parallel to each other, but also can be patterned perpendicular or at an angle. The patterns can also be non-symmetrical or irregular.

The first pattern 615 can be a different shape or pattern than the second pattern 620. The first pattern 615 and second pattern 620 could both partially cover certain areas of the protective areas 635. For example, the areas that experience the most diaper rash could be covered by both the first pattern and second pattern while areas that experience less diaper rash could be split between the diapers packaged together. When other shapes, such as dots, are used, the patterns are offset in order to cover the entire protective area 635 between the diapers packaged together.

Figure 7:
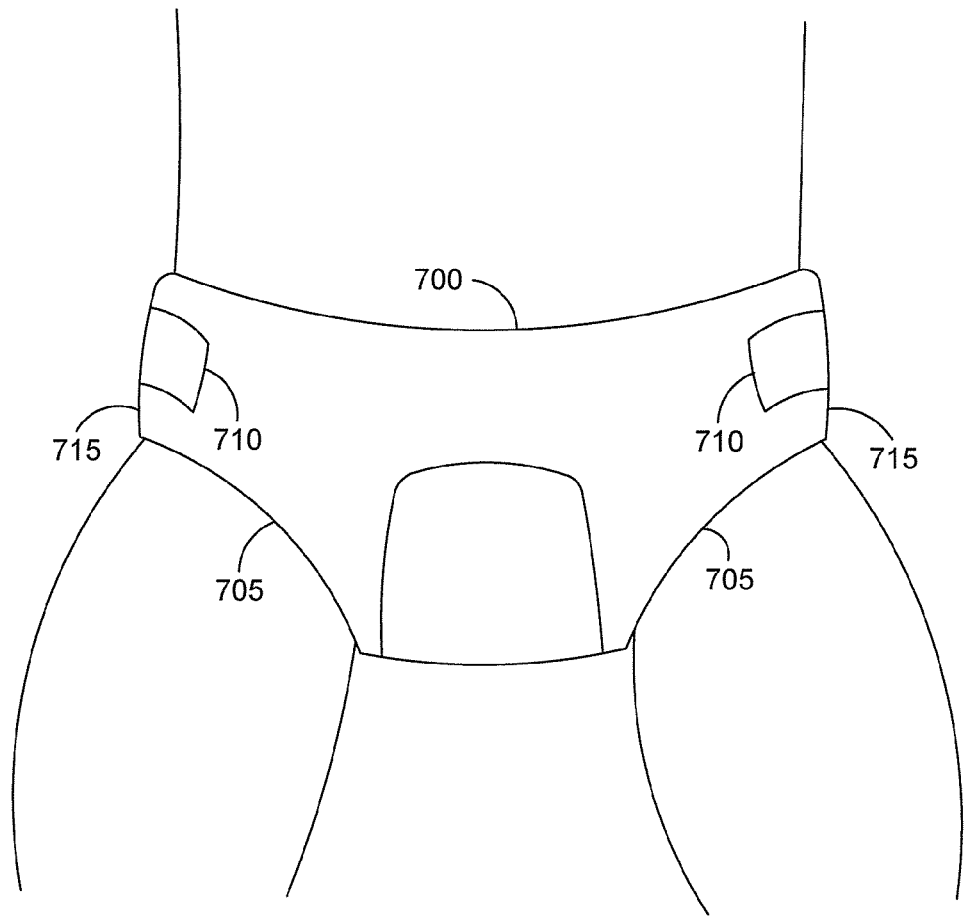
FIG. 7 illustrates a diaper worn on a wearer in accordance with disclosed embodiments.

FIG. 7 illustrates a diaper 700 worn on a wearer according to one embodiment of the present disclosure. The embodiment shown in FIG. 7 is for illustrations only. Other embodiments could be used without departing from the scope of the present disclosure.

For use of the diaper 700, the caregiver removes the enclosing layer exposing the topical layer. The caregiver places the diaper 700 on the baby with the leg linings 705 around the legs of the baby and connects the fasteners 710 to the tabs 715 on the front end of the diaper 700. The topical layer contacts the wearer and, for example, after 2-4 minutes of drying time, the topical layer melts to provide a calming effect on the wearer, for prevention or reduction of diaper rash. The diaper 700 can also include features such as color changing notification for changing, different designs or illustrations, different colors, or any other features found in diapers.

Figure 8:
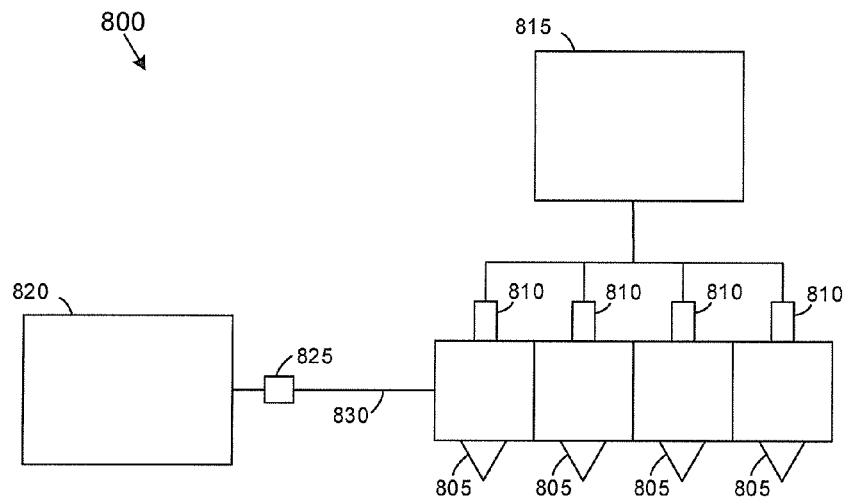
FIG. 8 illustrates a manufacturing assembly for producing a package of diapers in accordance with disclosed embodiments.

FIG. 8 illustrates a manufacturing assembly 800 for producing a package of diapers in accordance with disclosed embodiments. The embodiment shown in FIG. 8 is for illustrations only. Other embodiments could be used without departing from the scope of the present disclosure.

The manufacturing assembly 800 includes a plurality of extrusion heads 805, a plurality of solenoid valves 810, a programmable logic controller (PLC) 815, a heated tank 820, a pump 825, and a heated hose 830. The heated tank 820 stores and heats the topical wax. The topical wax is heated in the heated tank 820 to a liquid state for transfer through the heated hose 830 and the plurality of extrusion heads 805 to the diaper. A pump 825 pumps the liquid wax through the heated hose 830 to the plurality of extrusion heads 805. The pump 825 can be hydraulic or pneumatic. The plurality of extrusion heads 805 controls the flow of the liquid wax onto the diaper. Each of the extrusion heads 805 can be controlled separately by a solenoid valve 810. The plurality of solenoid valves 810 control the plurality of extrusion heads 805 in a manner that the liquid wax can be applied in different patterns and amounts. A PLC 815 controls the plurality of solenoid valves 810. The PLC 815 is programmed to operate the plurality of solenoid valves 810 to apply the pattern on each diaper. The PLC 815 applies the topical wax in a manner that over the use of a pack of diapers the entire affected area is covered.

Figure 9:
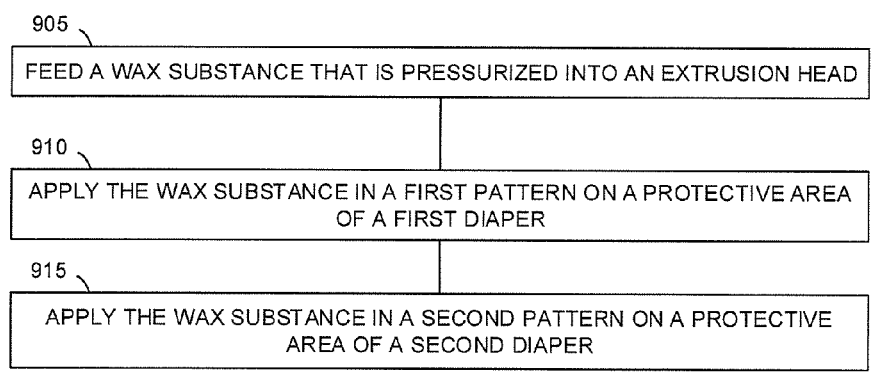
FIG. 9 illustrates a process for manufacturing a group of diapers in accordance with disclosed embodiments.

FIG. 9 illustrates a process for manufacturing a group of diapers in accordance with disclosed embodiments. The different operations of the process can be controlled by a processor executing instructions on a memory element.

In operation 905, the manufacturing system feeds a wax substance that is pressurized for use as a topical layer over a protective area for each of a plurality of diapers. The protective area is positioned on each of the plurality of diapers in a manner for consistent application on a wearer. In some embodiments, the protective area is fully within the area of the absorbent layer. The wax substance is pressurized by a hydraulic pump and applied in the first pattern and the second pattern through a plurality of extrusion heads In operation 910, the manufacturing system applies the wax substance in a first pattern on a protective area of a first diaper. The manufacturing system controls each of the plurality of extrusion heads using solenoid valves. The timing of the solenoid valves is controlled using a programming logic control (PLC) that is programmed to ensure every portion of the protective area is covered by either the first pattern on the first diaper or the second pattern on the second diaper.

In operation 915, the manufacturing system applies the wax substance in a second pattern on a protective area of a second diaper. The portions of the protective area of the first diaper not covered by the first pattern are covered by the second pattern on the protective area of the second diaper.

Although the present disclosure has been described with exemplary embodiments, various changes and modifications may be suggested to one skilled in the art. It is intended that the present disclosure encompass such changes and modifications as fall within the scope of the appended claims.

What is claimed is:

1. A package of diapers for treating diaper rash, the package of diapers comprising:
 a first diaper comprising:
  an absorbent layer configured to absorb moisture away from a wearer of the first diaper; and
  a topical layer applied to the absorbent layer of the first diaper in a first pattern,
  wherein the topical layer is a wax substance adapted to melt when the first diaper is used, and
  wherein the first pattern includes a number of individual portions of topical layer positioned on the absorbent layer, and
  wherein the first pattern is configured to prevent thickness of the wax substance when melted.

2. The package of diapers of claim 1, further comprising:
 a second diaper comprising:
  an absorbent layer configured to absorb moisture away from a wearer of the second diaper; and
  a topical layer applied of the absorbent layer of the second diaper in a second pattern;
  wherein the first pattern is different than the second pattern, and
  wherein the second pattern covers portions of the absorbent layer that correspond to portions of the absorbent layer of the first diaper that are not covered by the first pattern.

3. The package of diapers of claim 2, wherein the first pattern and the second pattern are applied as dots.

4. The package of diapers of claim 3, wherein the dots are applied in a matrix pattern.

5. The package of diapers of claim 4, wherein the second pattern of dots is offset from the first pattern of dots.

6. A diaper for treating diaper rash comprising:
 an absorbent layer configured to absorb moisture;
 a topical layer comprising organic shea butter, pure white beeswax, and a plurality of specialized ingredients,
 wherein the topical layer is a wax substance adapted to melt when the diaper is used, and
 wherein the topical layer is applied to the absorbent layer in a pattern that includes a number of individual portions of topical layer positioned on the absorbent layer, and
 wherein the first pattern is configured to prevent thickness of the wax substance when the wax substance is melted.

7. The diaper of claim 6, wherein the plurality of specialized ingredients comprise zinc oxide power, liquid lanolin, organic dandelion root powder and chickweed herb powder.

8. The diaper of claim 6, wherein the plurality of specialized ingredients comprise zinc oxide powder, liquid lanolin, organic aloe vera powder, and chamomile flowers.

9. The diaper of claim 6, wherein the plurality of specialized ingredients comprise zinc oxide power, liquid lanolin, cod liver oil, and chamomile flowers powder.

10. The diaper of claim 6, wherein the plurality of specialized ingredients comprise zinc oxide powder, cod liver oil, chickweed herb powder, liquid lanolin, and dandelion root powder.

11. The diaper of claim 6, wherein the plurality of specialized ingredients comprise 2% by weight of chickweed herb powder, 2% by weight of dandelion root powder, 40% by weight of zinc oxide powder, 4% by weight of cod liver oil, and 2% by weight of liquid lanolin.

12. The package of diapers of claim 1, wherein the absorbent layer comprises different areas of thickness adapted to guide the topical layer when melted.

13. The package of diapers of claim 12, wherein the different areas of thickness prevent the topical layer from concentrating when melted.

14. The package of diapers of claim 13, wherein a thickness at a center of the absorbent layer is reduced from outside edges of the absorbent layer.

\* \* \* \* \*